United States Patent
Henson

(10) Patent No.: US 11,356,353 B1
(45) Date of Patent: Jun. 7, 2022

(54) SYSTEM AND PROCESS TO PERFORM SYNTHETIC TESTING OF DIGITAL IMAGING AND COMMUNICATIONS IN MEDICINE DEVICES AND INTEGRATIONS IN A NETWORK

(71) Applicant: Kyle Matthew Henson, Lantana, TX (US)

(72) Inventor: Kyle Matthew Henson, Lantana, TX (US)

( * ) Notice: Subject to any disclaimer, the term of this patent is extended or adjusted under 35 U.S.C. 154(b) by 0 days.

(21) Appl. No.: 16/417,452

(22) Filed: May 20, 2019

(51) Int. Cl.
| | | |
|---|---|---|
| *G06F 15/173* | (2006.01) | |
| *H04L 43/50* | (2022.01) | |
| *G16H 30/20* | (2018.01) | |
| *H04L 43/04* | (2022.01) | |
| *H04L 43/0811* | (2022.01) | |

(52) U.S. Cl.
CPC ............. *H04L 43/50* (2013.01); *G16H 30/20* (2018.01); *H04L 43/04* (2013.01); *H04L 43/0811* (2013.01)

(58) Field of Classification Search
CPC ..... H04L 43/50; H04L 43/04; H04L 43/0811; G16H 30/20
See application file for complete search history.

(56) References Cited

U.S. PATENT DOCUMENTS

| | | | | | |
|---|---|---|---|---|---|
| 2005/0262200 | A1* | 11/2005 | Moritzen | ................ | H04L 69/40 709/204 |
| 2008/0208046 | A1* | 8/2008 | Pierce | .................... | A61B 8/565 600/437 |
| 2009/0161559 | A1* | 6/2009 | Bielig | ..................... | H04L 43/50 370/242 |
| 2012/0117205 | A1* | 5/2012 | Nolte | .................... | G06F 19/321 709/220 |
| 2014/0201341 | A1* | 7/2014 | Nolte | .................... | G06F 19/321 709/220 |

(Continued)

FOREIGN PATENT DOCUMENTS

DE 102010063129 A1 * 6/2012 ......... H04N 1/00031

OTHER PUBLICATIONS

DE102010063129 English Translation from Google Patents (Year: 2012).*

*Primary Examiner* — Richard G Keehn
(74) *Attorney, Agent, or Firm* — Hamilton, Brook, Smith & Reynolds, P.C.

(57) ABSTRACT

A system and process generate a closed loop test and transactions which removes the variable of lack of data and verifies that each system in the network is indeed moving data instead of simply showing that the software in the network is running. In some embodiments, a unique digital imaging and communications in medicine (DICOM) image is generated. The image may be retrieved from each system in the network so that individual network elements are tested. A new DICOM image may in some embodiments be generated and sent to a first system and retrieved from a second system in the network verifying the integration between the two connected systems. The sum of these tests may automatically monitor all devices in the overall system. The process may be automated so that system administrators may be notified when there is a problem via for example, an electronic dashboard, email or SMS text message.

7 Claims, 3 Drawing Sheets

(56) References Cited

U.S. PATENT DOCUMENTS

| | | | |
|---|---|---|---|
| 2015/0237106 A1* | 8/2015 | Golay | A61B 6/145 |
| | | | 709/203 |
| 2015/0256825 A1* | 9/2015 | Priest | H04L 43/0811 |
| | | | 348/181 |
| 2017/0220739 A1* | 8/2017 | Hammerle | H04L 41/14 |
| 2019/0215255 A1* | 7/2019 | Hashimoto | H04L 12/4625 |
| 2020/0168319 A1* | 5/2020 | Gragg | G06F 21/32 |
| 2020/0335198 A1* | 10/2020 | Accomazzi | G16H 30/20 |

* cited by examiner

SYSTEM AND PROCESS TO PERFORM SYNTHETIC TESTING OF DIGITAL IMAGING AND COMMUNICATIONS IN MEDICINE DEVICES AND INTEGRATIONS IN A NETWORK

CROSS-REFERENCE TO RELATED APPLICATIONS

None.

BACKGROUND

The embodiments herein relate generally to network testing and more particularly to, a system and process to perform synthetic testing of digital imaging and communications in medicine devices in a network.

The acquisition and display of medical images is complex and involves multiple discrete systems. When a problem occurs, the source of the problem may reside in any one of the systems involved or the integration between systems. Each individual system monitors itself but there are no tools or processes to test the entire chain of events or integrations between applications.

Current systems look to see if data is processing between systems, only if data is generated; for example such as when a patient gets an X-ray. They cannot differentiate between a system with no data moving because of an outage from a system with no data moving because there is no current transaction. When an administrator is notified of an issue today the administrator must trace an existing image backwards through all systems until the issues is found. In highly connected networks, this can be a time-consuming task.

SUMMARY

In one aspect, a computer program product for identifying a source of error in a digital imaging and communications in medicine (DICOM) network, comprises a non-transitory computer readable storage medium having computer readable program code embodied therewith. The computer readable program code is configured to: send a first unique test image file to a first network element in the DICOM network; retrieve an output file of the test image from the first network element; compare the output file to a reference file of the test image file; determine whether the output file of the first network element matches an expected result of the reference file; and determine whether the first network element is a source of error in the DICOM network based on the determination of the output file of the first network element matching the expected result of the reference file.

In another aspect, a process of identifying a source of error in a digital imaging and communications in medicine (DICOM) network comprises sending from a processor, a first message to a DICOM acquisition device checking for connectivity with the DICOM acquisition device, wherein the DICOM acquisition device is a machine that generates a medical-based image; sending from the processor, a test image file to a first network element in the DICOM network; retrieve, by the processor, an output file of the test image from the first network element; compare, by the processor, the output file to a reference file of the test image file; determine, by the processor, whether the output file of the first network element matches an expected result of the reference file; and determine, by the processor, whether the first network element is a source of error in the DICOM network based on the determination of the output file of the first network element matching the expected result of the reference file.

In yet another aspect, a process of identifying a source of error in a digital imaging and communications in medicine (DICOM) network comprises sending from a processor, a first message to a DICOM acquisition device checking for connectivity with the DICOM acquisition device, wherein the DICOM acquisition device is a machine that generates a medical-based image; sending from the processor, a test image file to a first network element in the DICOM network; retrieving, by the processor, an output file of the test image from a second network element connected to the first network element; comparing, by the processor, the output file of the second network element to the reference file of the test image file; determining, by the processor, whether the output file of the second network element matches the expected result of the reference file; and determining, by the processor, whether a connection between the first network element and the second network element is a source of error in the DICOM network based on the determination of the output file of the second network element matching the expected result of the reference file

BRIEF DESCRIPTION OF THE FIGURES

The detailed description of some embodiments of the invention is made below with reference to the accompanying figures, wherein like numerals represent corresponding parts of the figures.

DETAILED DESCRIPTION OF CERTAIN EMBODIMENTS

In general, embodiments of the disclosed invention provide system and process which generate a closed loop test and transactions which removes the variable of lack of data and verifies that each system is indeed moving data instead of simply showing that the software in the network is running. In some embodiments, a unique digital imaging and communications in medicine (DICOM) image is generated. The image may be stored in and retrieved from each system in the network so that individual systems are tested. In some embodiments, a new DICOM image may be generated and sent to a first system and retrieved from a second system in the network verifying the integration between the two connected systems. The sum of these tests may automatically monitor all devices in the overall system. Process may be automated so that system administrators may be notified when there is a problem via for example, an electronic dashboard, email or SMS text message. As will be appreciated, aspects disclosed herein reduce overall operational downtimes by rapidly detecting a problem and focusing on troubleshooting efforts. The system and process may also be used internally by other software vendors to detect integration issues internally between devices such as in a commercial picture archive communication system (PACS). In an industrial application, embodiments may be used in in a hospital to monitor the end to end data flow for images. Some aspects may also be used to monitor remote systems that are used sporadically such as in a Teleradiology operation, to ensure that a rarely used system is operational when data is not organically sent.

Figure 1:
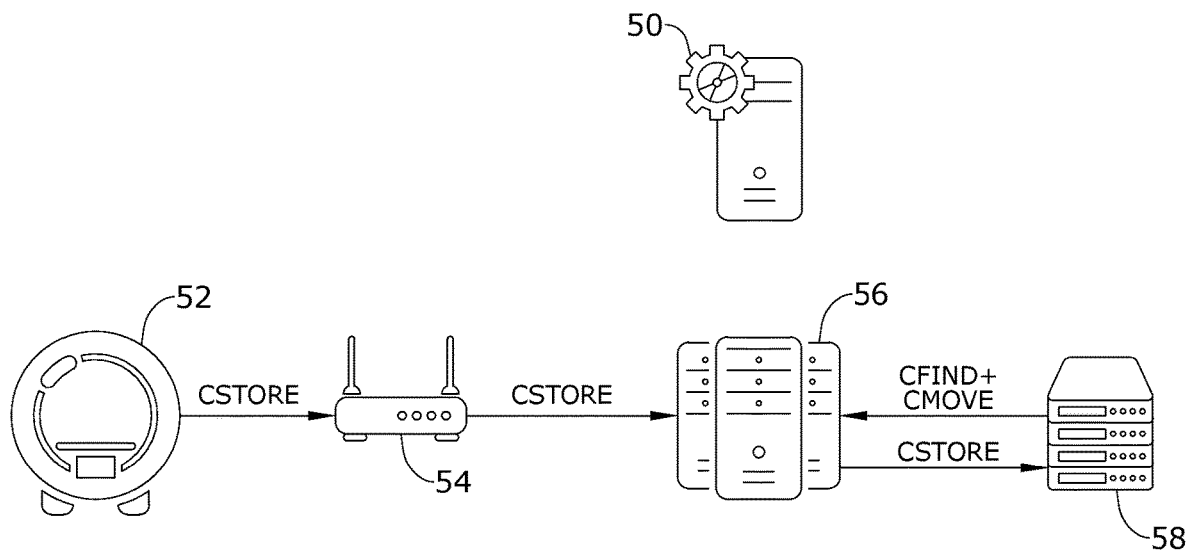
FIG. 1 is a schematic diagram of a network and process for acquiring data for DICOM connected devices according to an embodiment.

Referring now to FIG. 1, a network and flow implementing a process according to an exemplary embodiment is shown. The system generally includes a computing device 50 which may be loaded up with a software product running process embodiments. The computing device 50 may be generally connected to other elements in the network by either hard wiring (for example, through an Ethernet connection) or by wireless connectivity. A network may also generally include a plurality of network connected DICOM devices. For example, a DICOM acquisition device 52, a DICOM router 54, a Picture Archive Communication System (PACS) 56, and a Vendor Neutral (image) Archive (VNA) 58 are shown in an exemplary network. The DICOM acquisition device 52 may be a machine that generates a medical image. Examples of a DICOM acquisition device include CT scan machines, MM machines, and Ultrasound machines. A PACS may comprise one or more computer servers.

As will be understood, sometimes as used, a "system" may describe individual network elements called out in the diagrams. Some of the network elements while represented by a single icon, may in reality represent several machines connected together for a specific function. For example, a PACS 56 may represent a plurality of computer servers connected to together (in some embodiments, in a cloud-based environment). A VNA 58 may represent a plurality of servers and databases connected together.

In FIG. 1, the process shown may be generally represent how DICOM files are generated and stored in a DICOM network. The DICOM acquisition device 52 generates a medical image file. When a CSTORE request in the system is made, the file may be forwarded through the DICOM router 54 to the PACS 56. The file may be stored in the VNA 58 until a CFIND+CMOVE command is triggered in the system (for example, by the PACS 56) which issues a retrieval of the file from the VNA 58. As will be appreciated, each stage of interaction between the elements in the network is a potential point for the file to be modified, corrupted, or generally transferred between elements in an erroneous format. Each network connected element may read the medical image's file in a different language format, which may require conversion between elements. Should the conversion be improperly performed, the result may generate a failure in the system when a request to retrieve the file is made. The source of the failure may be the file, however, the file may be a symptom of a network element operating incorrectly. Isolating the location of the error source in a complex network may be provided by the embodiments described herein.

Figure 2:
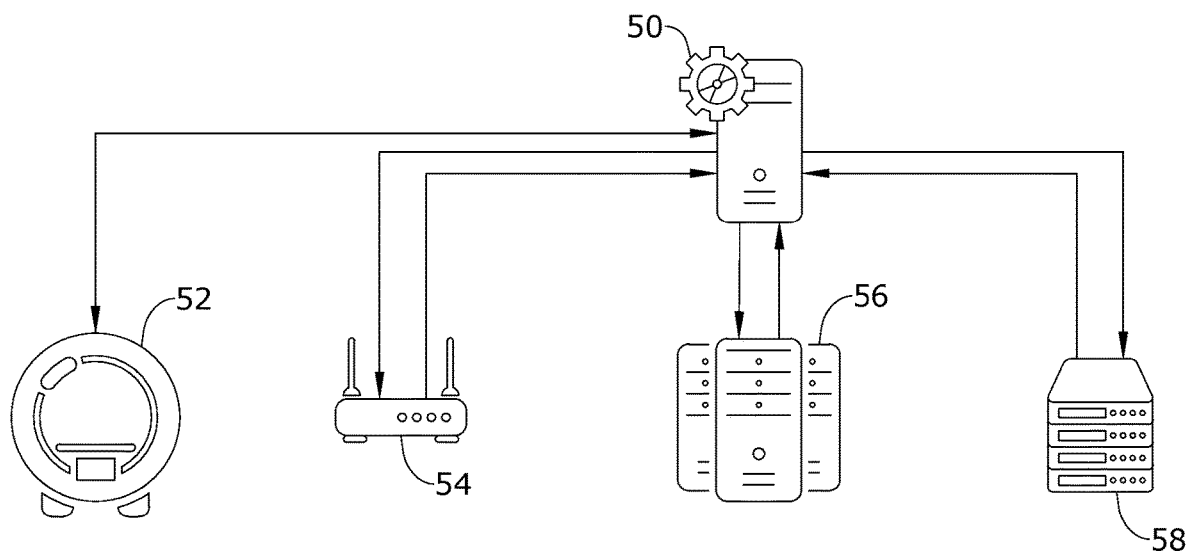
FIG. 2 is a schematic diagram of a network using a synthetic testing process in a network of DICOM connected devices according to an exemplary embodiment.

Referring now to FIG. 2, a process for identifying operational status of a network element is shown according to an exemplary embodiment. The computing device 50 device may use transactions and synthetic data to test each system in the network. Synthetic test data may be a surrogate file configured solely as a reference file to check for the operational status of a network connected device. Synthetic test data may be for example, a file that is generated from arbitrary data or pulled from a stored file that is not necessarily an actual medical file of a subject generated by the system. In general, the process may periodically test the network for each connected element's operational status and its ability to correctly move and store data.

The computing device 50 may send a C-ECHO command transaction message to the DICOM acquisition device 52 checking for connectivity. If the connectivity check shows a lack of communication, a first troubleshooting step may begin at the DICOM device 52. Should connectivity be present, independently and on a schedule, the process may send a unique image (synthetic data) via a CSTORE request to the DICOM router 54. The process may retrieve the same image via a CFIND+CMOVE commands verifying that the DICOM router 54 is functional. An error may be triggered if the image is not returned matching a stored copy of the image in a reference file. The process may continue by sending the unique image via a CSTORE command and then retrieving the image for each device in the network. For example, the image may be sent to the PACS 56 and the VNA 58 and the returned result for each may be compared to the reference file of the unique image. For each network device tested, if the image is retrieved successfully the system is functional. If a test results in the image not being able to be retrieved or does not match the image stored, an alert may be generated, and users notified.

Figure 3:
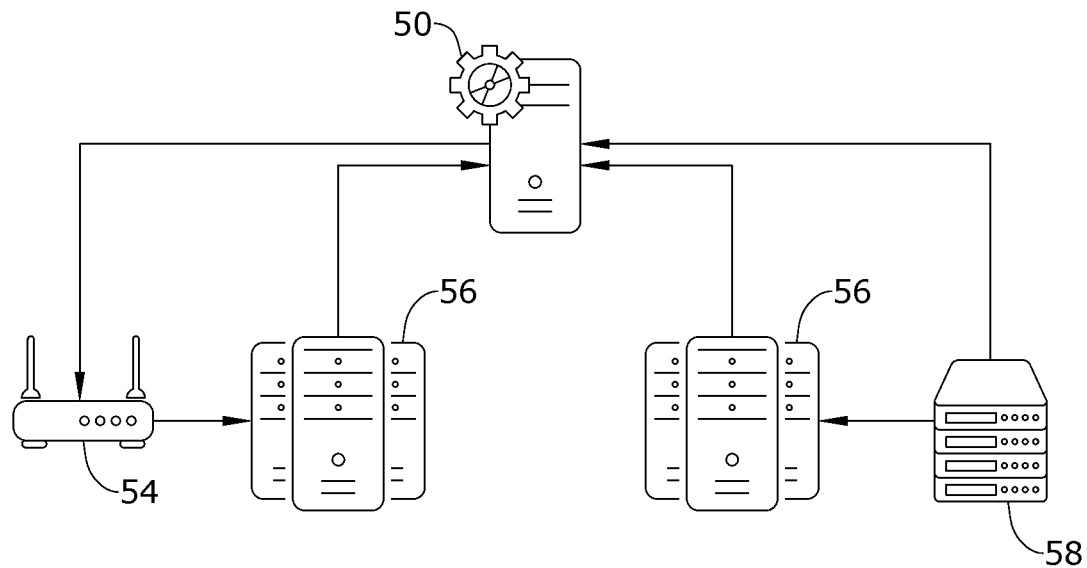
FIG. 3 is a schematic diagram of a network using a synthetic testing process in a network of DICOM connected devices according to an exemplary embodiment.

Referring now to FIG. 3, a process for identifying a source of error in a network is shown according to another embodiment. The process shown is similar to the process in FIG. 2 except that instead of checking each network element/system individually, the process may compare the transfer of files between groups of connected systems to check for flaws in the interface between elements. In the system shown, while two PACs 56 are shown, the PACs 56 may represent the same PACs being evaluated or may represent discrete PACS connected to the network. The process shown is checking for communication results between the PACs 56 and the DICOM router 54 and VNA 58. In general, the generated test image file is retrieved from the second network element and compared thus verifying if the integration between the first network element and the second network element is the source of the error. The process may send a unique test image (synthetic data) to the DICOM router 54, which then transfers the test image to the PACs 56. The originating computing device 50 uses requests by CFIND, CMOVE commands to obtain the output from the PACs 56 and compares the file obtained to the reference file. Similarly, the computing device 50 may send a unique test image to the PACs 56 which may then transfer the test mage data to the VNA 58. The copy of the test image in the VNA 58 may be retrieved by the computing device 50 and compared to the reference file for validity of the content therein.

Figure 4:
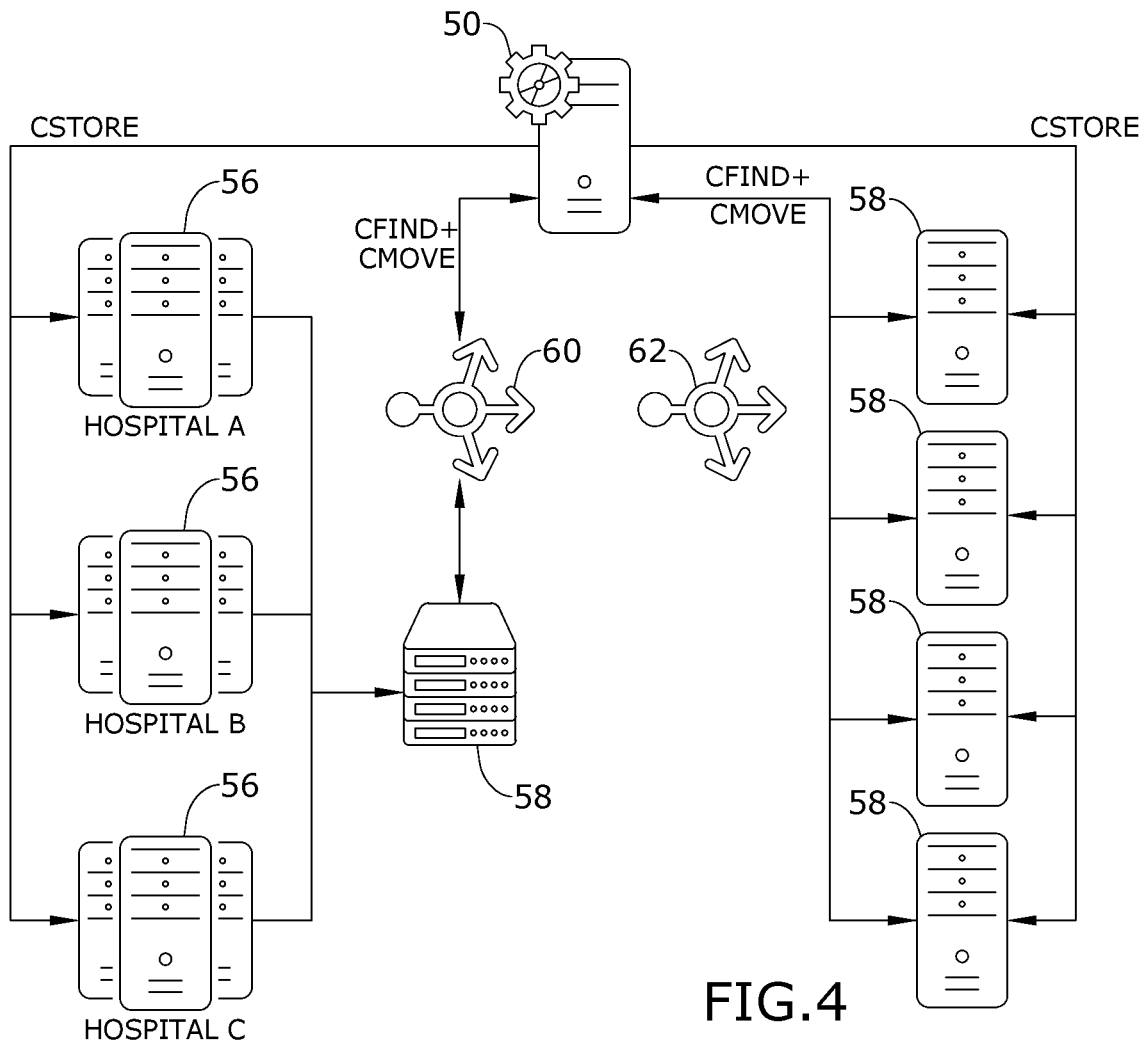
FIG. 4 is a schematic diagram of a network using a synthetic testing process in a network of DICOM connected devices according to an exemplary embodiment.

Referring now to FIG. 4, embodiments of the process is shown in a more complex network. As will be appreciated, the network example shown illustrates how many more actual elements may be present, including on a macro level, how multiple facilities (for example, hospitals) may all be connected to the same network. The left side of the diagram shows multiple hospitals "A", "B", and "C" and their individual PACs 56 being tested in the aggregate. A CSTORE command with unique the test images may be sent from the computing device 50 to each of the PACs 56. The PACs 56 may access a shared VNA 58 each storing their test images to the archival files. A CFIND+CMOVE request may retrieve the stored test images from the VNA 58 through a VNA load balancer 60. A comparison of the files retrieved through the VNA load balancer 60 may be compared to the reference files. On the right side of the diagram, a different implementation of the process is shown. The right side of the diagram may represent testing individual computer servers (for example VNA servers 58). The CSTORE command with a unique test image may be sent to each individual servers 58. A CFIND+COMOVE request for the test image may be sent to individual servers 58 whose output may bypass the VNA load balancer 62 en route to the computing device 50 for comparison of the retrieved file to the reference file.

As will be appreciated, a source of error in the movement of image data or processing of image data may be isolated by use of the synthetic data file to test what the output of each connected element or groups of elements provide. Such an approach improves time involved in tracking down why images are unavailable or being generated with errors.

Figure 5:
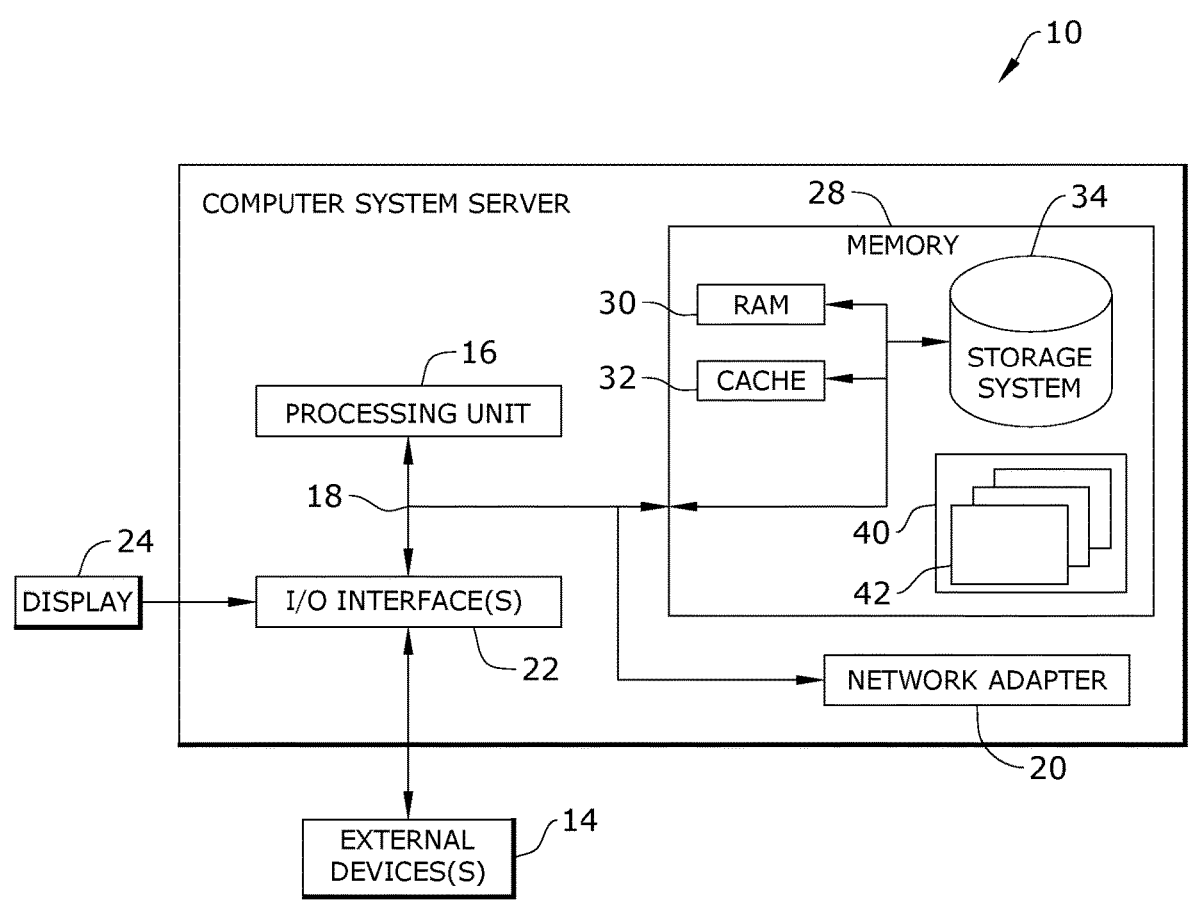
FIG. 5 is a block diagram of a computer system/server according to an embodiment of the subject technology.

Referring now to FIG. 5, a schematic of an example of a computer system/server 10 is shown. The computer system/server 10 is shown in the form of a general-purpose computing device. The computing device 10 may represent the computing device 50 as well as one or more network connected elements (for example, the PACs 56 or VNA 58). In some embodiments, the DICOM acquisition device 52 may be integrated with a computing device 50. Thus, description of the computer system/server 10 may represent functionality also present in one or more of the network connected elements described above.

The components of the computer system/server 10 may include, but are not limited to, one or more processors or processing units 16, a system memory 28, and a bus 18 that couples various system components including the system memory 28 to the processor 16.

The computer system/server 10 may perform functions as different machine types depending on the role in the system the function is related to. For example, as a network administrator interface with the system, the computer system/server 10 may be for example, personal computer systems, tablet devices, mobile telephone devices, server computer systems, handheld or laptop devices, multiprocessor systems, microprocessor-based systems, programmable consumer electronics, network PCs, and distributed cloud computing environments that include any of the above systems or devices, and the like. The computer system/server 10 may be described in the general context of computer system executable instructions, such as program modules, being executed by a computer system (described for example, below). In some embodiments, the computer system/server 10 may be a cloud computing node connected to a cloud computing network (not shown). The computer system/server 10 may be practiced in distributed cloud computing environments where tasks are performed by remote processing devices that are linked through a communications network. In a distributed cloud computing environment, program modules may be located in both local and remote computer system storage media including memory storage devices.

The computer system/server 10 may typically include a variety of computer system readable media. Such media could be chosen from any available media that is accessible by the computer system/server 10, including non-transitory, volatile and non-volatile media, removable and non-removable media. The system memory 28 could include one or more computer system readable media in the form of volatile memory, such as a random access memory (RAM) 30 and/or a cache memory 32. By way of example only, a storage system 34 can be provided for reading from and writing to a non-removable, non-volatile magnetic media.

The system memory 28 may include at least one program product 40 having a set (e.g., at least one) of program modules 42 that are configured to carry out the functions of embodiments of the invention. The program product/utility 40, having a set (at least one) of program modules 42, may be stored in the system memory 28 by way of example, and not limitation, as well as an operating system, one or more application programs, other program modules, and program data. Each of the operating system, one or more application programs, other program modules, and program data or some combination thereof, may include an implementation of a networking environment. The program modules 42 generally carry out the functions and/or methodologies of embodiments of the invention as described above including for example, processes of generating synthetic data, issuing C-ECHO, CSTORE, CFIND, and CMOVE commands, comparing retrieved files to reference files and determining whether a retrieved file matches a reference file for purposes of identifying a location/source of error in the network.

The computer system/server 10 may also communicate with one or more external devices 14 such as a keyboard, a pointing device, a display 24, etc.; and/or any devices (e.g., network card, modem, etc.) that enable the computer system/server 10 to communicate with one or more other computing devices. Such communication can occur via Input/Output (I/O) interfaces 22. Alternatively, the computer system/server 10 can communicate with one or more networks such as a local area network (LAN), a general wide area network (WAN), and/or a public network (e.g., the Internet) via a network adapter 20. As depicted, the network adapter 20 may communicate with the other components of the computer system/server 10 via the bus 18.

As will be appreciated by one skilled in the art, aspects of the disclosed invention may be embodied as a system, method or process, or computer program product. Accordingly, aspects of the disclosed invention may take the form of an entirely hardware embodiment, an entirely software embodiment (including firmware, resident software, microcode, etc.) or an embodiment combining software and hardware aspects that may all generally be referred to herein as a "circuit," "module," or "system." Furthermore, aspects of the disclosed invention may take the form of a computer program product embodied in one or more computer readable media having computer readable program code embodied thereon.

Any combination of one or more computer readable media (for example, storage system 34) may be utilized. In the context of this disclosure, a computer readable storage medium may be any tangible or non-transitory medium that can contain, or store a program (for example, the program product 40) for use by or in connection with an instruction execution system, apparatus, or device. A computer readable storage medium may be, for example, but not limited to, an electronic, magnetic, optical, electromagnetic, infrared, or semiconductor system, apparatus, or device, or any suitable combination of the foregoing.

Aspects of the disclosed invention are described below with reference to block diagrams of methods, apparatus (systems) and computer program products according to embodiments of the invention. It will be understood that each block of the block diagrams, and combinations of blocks in the flowchart illustrations and/or block diagrams, can be implemented by computer program instructions. These computer program instructions may be provided to the processor 16 of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

Persons of ordinary skill in the art may appreciate that numerous design configurations may be possible to enjoy the functional benefits of the inventive systems. Thus, given the wide variety of configurations and arrangements of embodiments of the present invention the scope of the invention is reflected by the breadth of the claims below rather than narrowed by the embodiments described above.

What is claimed is:

1. A computer program product for identifying a source of error in a digital imaging and communications in medicine (DICOM) network, the computer program product comprising a non-transitory computer readable storage medium having computer readable program code embodied therewith, the computer readable program code being configured to:
   send, from a network administrator interface computing device, a C-ECHO command to a DICOM acquisition device, wherein the DICOM acquisition device is a machine that generates a medical-based image;
   verify the connectivity of the DICOM acquisition device in the DICOM network from a result of the C-ECHO command;
   generate, in the network administrator interface computing device, a first unique test image file from synthetic data comprising arbitrary DICOM-based data;
   send, from the network administrator interface computing device, the first unique test image file to a first network element in the DICOM network, the first network element in operative arrangement with a second network element in the DICOM network;
   retrieve by the network administrator interface computing device an output image file corresponding to the first unique test image file from the second network element using a CFIND+CMOVE command;
   compare the output image file to the first unique test image file;
   determine whether the output image file of the second network element matches the arbitrary DICOM-based data of the synthetic data; and
   determine whether the first DICOM acquisition device, the first network element, or the second network element is a source of error in the DICOM network based on the determination of the output image file of the second network element matching the arbitrary DICOM-based data of the synthetic data.

2. The computer program product of claim 1, further comprising computer readable program code being configured to:
   send a second unique test image file to the second network element in the DICOM network;
   retrieve an output image file of the second unique test image from the second network element;
   compare the output image file of the second network element to the arbitrary DICOM-based data of the synthetic data;
   determine whether the output image file of the second network element matches the arbitrary DICOM-based data of the synthetic data; and
   determine whether the second network element is the source of error in the DICOM network based on the determination of the output image file of the second network element matching the arbitrary DICOM-based data of the synthetic data.

3. The computer program product of claim 2, wherein the computer readable program code is configured to:
   automatically send the first and second unique test image files to the first and second network elements on a scheduled basis.

4. The computer program product of claim 2, wherein the DICOM acquisition device is the first network element.

5. The computer program product of claim 1, wherein the DICOM acquisition device is a computed tomography (CT) scan machine, a magnetic resonance imaging (MRI) machine, or an ultrasound machine (US).

6. A process of identifying a source of error in a digital imaging and communications in medicine (DICOM) network, comprising:
   sending, from a processor, a first message to a DICOM acquisition device checking for connectivity with the DICOM acquisition device, wherein the DICOM acquisition device is a machine that generates a medical-based image;
   generating a unique test image file;
   sending, from the processor, the unique test image file to a first network element in the DICOM network, the first network element in operative arrangement with a second network element in the DICOM network;
   retrieving, by the processor, an output image file corresponding to the unique test image file from the first network element, wherein the unique test image file is read by the first network element in a first format;
   comparing, by the processor, the output image file corresponding to a reference file of the unique test image file;
   determining, by the processor, whether the output image file of the DICOM acquisition device first network element matches an expected result of the reference file;
   retrieving, by the processor, an output image file corresponding to the unique test image file from the second network element, wherein the unique test image file is read by the second network element in a second format that is different than the first format;
   determining whether the output image file corresponding to the unique test image file from the second network element matches the expected result of the reference file; and
   determining, by the processor, whether the DICOM acquisition device, the first network element, or the second network element is a source of error in the DICOM network based on the determination of the output files of the first and second network elements matching the expected result of the reference file.

7. The process of claim 6, wherein the processor automatically sends the unique test image file to the first and second network elements on a scheduled basis.

* * * * *